(12) United States Patent
Koshti et al.

(10) Patent No.: US 7,147,866 B2
(45) Date of Patent: Dec. 12, 2006

(54) UV-ABSORBING LIPID VESICLES

(75) Inventors: Nirmal Madhukar Koshti, Maharashtra (IN); Shubhangi Dattaram Naik, Maharashtra (IN); Tanaji Shamrao Jadhav, Maharashtra (IN)

(73) Assignee: Galaxy Surfactants Limited, Maharashtra (IN)

( * ) Notice: Subject to any disclaimer, the term of this patent is extended or adjusted under 35 U.S.C. 154(b) by 118 days.

(21) Appl. No.: 10/953,832

(22) Filed: Sep. 29, 2004

(65) Prior Publication Data

US 2006/0067893 A1 Mar. 30, 2006

(51) Int. Cl.
*A61K 9/127* (2006.01)
*C07C 233/00* (2006.01)
*A61K 31/165* (2006.01)

(52) U.S. Cl. .................. 424/450; 564/163; 564/168; 564/170; 564/182; 514/619; 514/622

(58) Field of Classification Search .............. None
See application file for complete search history.

(56) References Cited

U.S. PATENT DOCUMENTS 5,427,773 A * 6/1995 Chaudhuri et al. ........... 424/60
5,451,394 A * 9/1995 Chaudhuri et al. ........... 424/60
5,601,811 A * 2/1997 Gallagher et al. .......... 424/709
6,613,340 B1 * 9/2003 Koshti et al. ............... 424/401

* cited by examiner

*Primary Examiner*—Brian Davis
(74) *Attorney, Agent, or Firm*—Akerman & Senterfitt; Stephan Pendorf

(57) ABSTRACT

Highly effective vesicular compositions from UV-absorbing lipids are described in the present invention. Combination of UV-absorbing property and the vesicular delivery system results in higher levels of photoprotection to skin and hair. The vesicular compositions of the present invention are made from cationic UV-absorbing lipids of Formula I wherein,

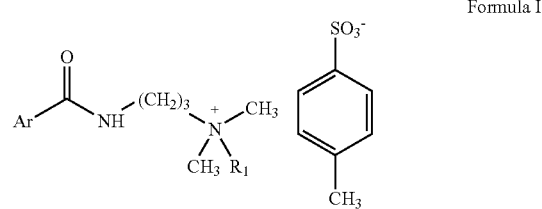

Formula I ArCO is selected from cinnamoyl, p-methoxy cinnamoyl, p-N,N-dimethylamino benzoyl and combinations thereof, $R_1$ is selected from saturated or unsaturated alkyl group with carbons ranging from $C_{10}$ to $C_{22}$.

6 Claims, 3 Drawing Sheets

FIG.1
FIG.2
FIG.3
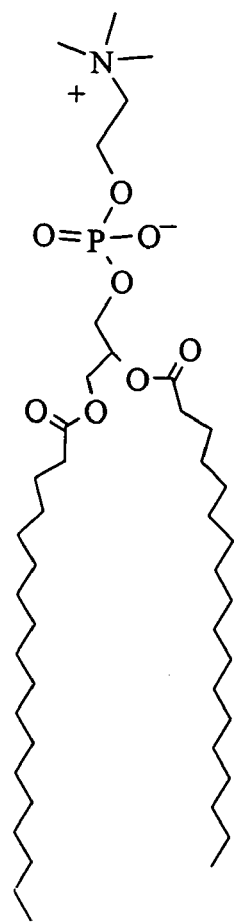
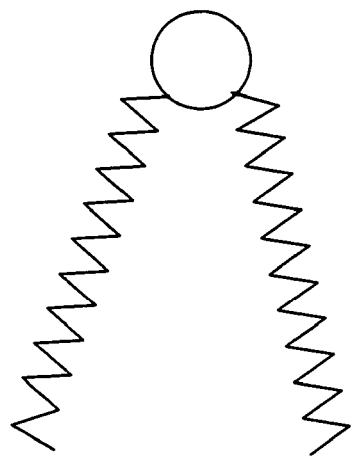
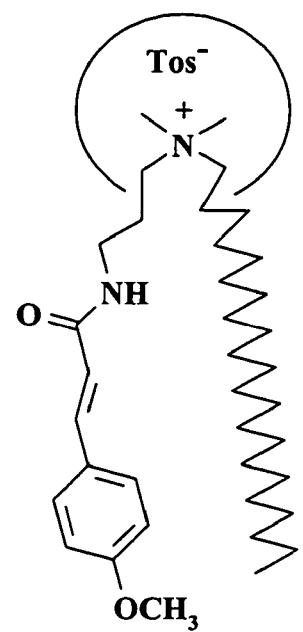

Electron Micrograph 1

UV-ABSORBING LIPID VESICLES

FIELD OF INVENTION

The invention relates to vesicles (liposomes) made, from UV-absorbing lipids. The lipids are quaternary ammonium type of amphiphiles containing cinnamido or benzamido moieties for UV-absorption. The vesicular (liposomal) dispersions of these lipids are effective in protecting skin and hair from UV radiation. These vesicles are useful in protecting active ingredients of a formulation and delivering them effectively in a personal care application. The invention is based on the fundamental cognition of the fact that UV-absorbing quaternary ammonium tosylates like cinnamidopropyl dimethyl alkyl ammonium tosylates and benzamidopropyl dimethyl alkyl ammonium tosylates form stable vesicles.

BACKGROUND AND PRIOR ART

Vesicle (liposome) formation is a natural result of the amphiphilic nature of certain molecules. Amphiphilic molecules are the ones which have both hydrophilic and hydrophobic portions in the same molecule. For molecules in which the cross sectional area of the hydrophilic region is slightly less or equal to hydrophobic part of the molecule then the formation of bilayers is favored as seen in case of many phospholipids. Liposomes are formed by folding of these bilayers of amphiphilic molecules. They may be formed as a single bilayer enclosing a single aqueous space or they may be composed of concentric bilayers with many aqueous spaces alternating with bilayers (multilamellar vesicles). Liposomes can be used to encapsulate both hydrophobic and hydrophilic materials. Hydrophobic payloads are typically partitioned within the bilayers, whereas hydrophilic payloads are typically trapped within the aqueous compartment. The advantages of using liposomes as carrier/encapsulation systems are that they are stable and can protect their payload from degradation. Thus, in summary, the liposomes have been shown to be useful in (i) solubilising of both lipophilic as well as hydrophilic active compounds, (ii) protection of these active ingredients by encapsulation, (iii) prolonging action by slow release of active compounds and (iv) delivering active compounds to the specific target tissue.

Vesicles obtained from phospholipids have been used for timed delivery of a wide variety of materials including cosmetics, nutrients and pharmaceuticals. For example, U.S. Pat. No. 4,016,100 (1977) discloses a method of producing pharmaceutical composition comprised of an aqueous suspension of active ingredient entrapped in a spherule of a phospholipid. U.S. Pat. No. 3,957,971 (1976) discloses moisturizing liposomes wherein a humectant is in aqueous space of the vesicle. In addition to phospholipids, non-ionic amphiphiles have also been used. For example, U.S. Pat. No. 4,772,471 (1988) discloses liposomal spherules from non-ionic lipids to encapsulate pharmaceutically or cosmetically active substances. Recently, cationic liposomes from alkyl ammonium fatty acid salts for encapsulating both hydrophilic and hydrophobic loads have been provided by U.S. Pat. No. 6,071,535 (2000).

The harmful effects of solar UV-radiation on skin are well known. The UV-B (290–320 nm) portion of solar spectrum is largely responsible for erythema (sunburn) and cancer. [M. M. Rieger, Cosmet. Toiletries, 102 (3), 91, (1987); L. Taylor, Skin Cancer Foundation J., 4, (90) (1986)].

Similarly, photodegradative effect of UV-radiation on human hair is well documented. Continuous exposure to sunrays lightens hair color and makes human hair rough, brittle and difficult to comb. UV rays are reported to damage the proteins of cuticles. Prolonged irradiation results in diminished tensile strength due to breaking of disulphide bonds in keratin. [R. Beyak et al, J. Soc. Cosmet. Chem. 22, 667–668 (1971), E. Hoting et al, J. Soc. Cosmet. Chem. 46, 85–99 (1995)].

It is fairly established that the quaternary ammonium type of UV-absorbers are more substantive to both hair and skin than their non-quaternised counterparts. This superior substantivity is the result of interaction of cationic centres with the keratin of skin and hair. There are number of reports in literature describing this aspect of quaternary UV-absorbing molecules. [Saettone, M. F.; Giannaccini, B.; Morganti, C.; Persi, A.; Cipriani, C. Int. J. Cosmet. Sci., 8(1), 9–25, (1986), U.S. Pat. No. 5,427,773 (1995), U.S. Pat. No. 5,601,811 (1997), U.S. Pat. No. 6,613,340 (2003)]

SUMMARY OF THE INVENTION

Though the quaternised UV-absorbers are more effective than the conventional non-quaternised ones, their photoprotection efficacy can still further be enhanced by converting them into vesicles. The present patent application discloses liposomal compositions made from UV-absorbing lipids that are capable of forming bilayers. Thus, the vesicles of the present invention can not only protect and deliver an active ingredient but they themselves offer protection to hair, skin and the encapsulated active ingredient from damages of UV-radiation. It further discloses that liposomal UV-absorbers are more efficient than the conventional UV-absorbers that do not form vesicles.

The present invention overcomes the problem of low loading of organic sunscreens in vesicles made from conventional lipids like phospholipids, ceramides, neosomes because the vesicles reported herein are themselves UV absorbing.

Hitherto, there are no literature reports on liposomal compositions of UV-absorbing lipids for protecting and delivering an active ingredient for topical application and protecting skin and hair by virtue of themselves being UV-absorbing.

The present invention relates to vesicle (liposome) compositions for hair and skin care comprising from 0.1 to 20% by weight of cationic UV-absorbing lipids of Formula I

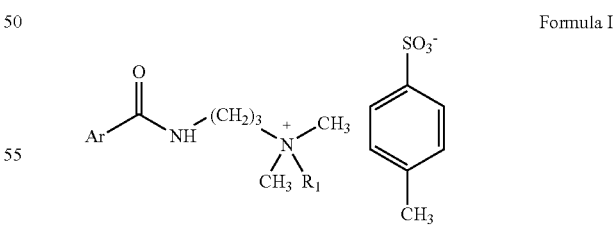

Formula I wherein
ArCO is selected from cinnamoyl, p-methoxy cinnamoyl, p-N,N-dimethylamino benzoyl and combinations thereof,
$R_1$ is selected from saturated or unsaturated alkyl group with carbons ranging from $C_{10}$ to $C_{22}$, wherein
the diameter of the vesicles range from 50 nm to 20 µm, said vesicles are substantive to hair and skin and are with or without skin actives or hair actives, and encapsulate the aqueous phase.

According to another embodiment of the invention there is provided a process for the preparation of the vesicle composition comprising (a) dispersing the cationic UV-absorbing lipid of formula I in water or buffer solution by sonication and (b) subjecting the dispersion to high shear mixing.

BRIEF DESCRIPTION OF THE DRAWINGS

In the following the invention will be described in detail with reference to the figures, wherein:

FIG.1. depicts a drawing of a typical phospholipid, phosphatidyl choline that forms liposomes (vesicles).

FIG.2. depicts the same phospholipid that has a hydrophilic head and two hydrophobic tails, FIG.3. is the structural formula for p-methoxy cinnamidopropyl dimethyl behenyl ammonium tosylate that brings out the resemblance between the vesicle forming quaternized UV absorber and a typical vesicle forming amphiphile with a hydrophilic head and two hydrophobic tails, FIG.4. demonstrates the aggregation of amphiphiles to form unilamellar vesicle, and FIG.5. is the transmission electron micrograph of vesicles derived from the quaternized UV absorbing lipid of FIG. 3.

DETAILED DESCRIPTION OF THE INVENTION

The purpose of this invention is to provide cationic vesicles from UV-absorbing lipids to achieve higher levels of protection to skin and hair from damaging solar radiation. These cationic liposomes lodge themselves in the upper layer of skin (stratum corneum) because of their lipidic bilayer nature that is quite similar to cell membrane of a living tissue. The cationic liposomes also have special affinity to the corneocytes of stratum corneum which are non-nucleated cells with plenty of keratin. Another significant fact is that the nanosize of cationic liposomes results in ease of penetration in the stratum corneum and into the intracellular lipids.

Thus, the penetration in the stratum corneum of skin by the cationic UV-absorbing liposomes is quite superior to non-liposomal UV-absorber. This is demonstrated by measuring the reduction of melanin generation by applying liposomal and non-liposomal UV-absorber. The cationic vesicles of the present invention are not only more substantive to skin but they are more penetrative as well. These nano size liposomes also serve as nano capsules for loading both water-soluble and lipid soluble active ingredients that need to be protected from UV-radiation (e.g. ascorbic acid, vitamin A and vitamin E). These active ingredients can be more effectively delivered in the skin layer through liposomes and thereby enhancing their efficacy as well as reducing their dosage level in the composition.

Figure 4:
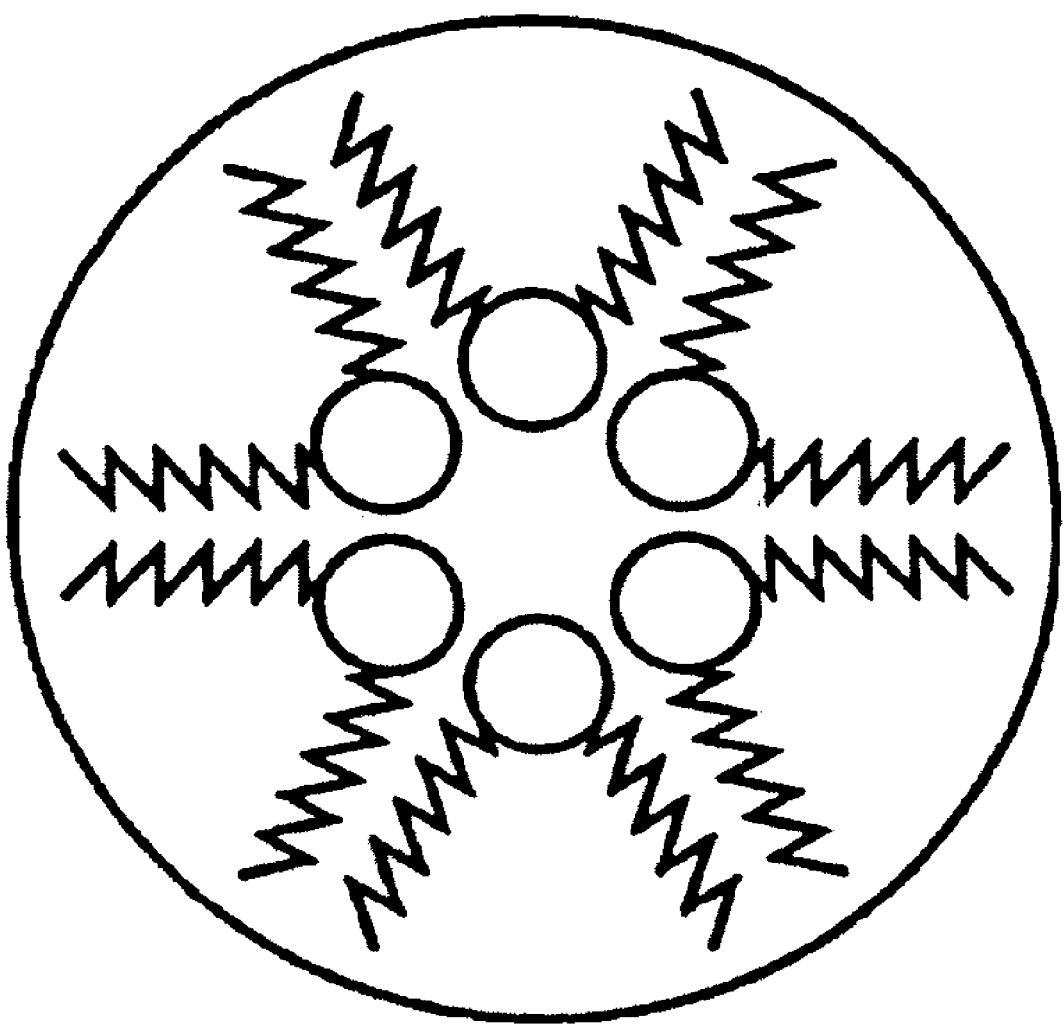

Phospholipids like phosphatidyl choline (lecithin, FIG. 1) form bilayers and liposomes. Lecithin, an amphiphile has a polar head group and two non-polar hydrophobic carbon chains (FIG. 2). A cationic UV-absorber like p-methoxy cinnamidopropyl dimethylalkyl ammonium tosylate (FIG. 3) can be looked upon as a two tailed amphiphile. A two tailed amphiphile like lecithin forms a unilamellar liposome in aqueous medium as shown in FIG. 4. Thus, in the similar manner, the cationic UV-absorbing molecules that meet the requirement of hydrophobicity and hydrophilicity can form bilayers and liposomes. The cationic UV-absorbing amphiphiles of Formula I are prepared according to the process described in U.S. patent application Ser. No. 10/682, 004 (2003). These UV-absorbing cationic lipids of Formula I are then converted into liposomes by known methods such as mechanical agitation, high shear mixing and sonication. The formation of liposomes has been confirmed by electron microscopy. On human skin, photoprotection efficacy of liposomal UV-absorber has been shown to be vastly superior then non liposomal UV-absorber.

The cationic UV-absorbers that are used in vesicles of the present invention contain cinnamido and benzamido moieties for UV-absorption. They are synthesized by a two step procedure, a) synthesis of quaternary ammonium halides of Formula IV and b) conversion of water-soluble quaternary ammonium halides of Formula IV to water-insoluble quaternary ammonium tosylates of Formula I [U.S. Pat. No. 6,613,340 (2003)].

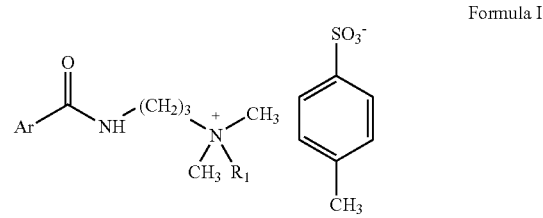

Formula I

The UV-absorbing cinnamidoalkylamines or benzamidoalkylamines of Formula II are synthesised as per the literature procedures [U.S. Pat. No. 5,427,773 (1995), U.S. Pat. No. 6,613,340 (2003)]. These amidoamines are quaternised using commercially available alkyl halides of Formula III in aqueous or alcoholic medium to give quantitative generation of corresponding water-soluble, UV-absorbing, quaternary ammonium halides of Formula IV. The quaternary ammonium tosylates of Formula I are obtained by reacting aqueous solutions of quaternary ammonium halides of Formula IV with sodium tosylate.

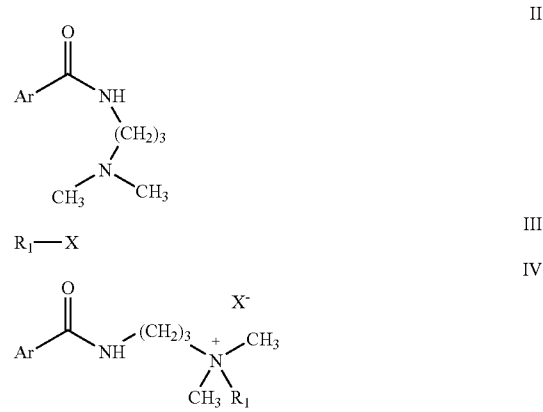

Another embodiment relates to liposomal preparation from cationic UV-absorbing lipids of Formula I, wherein ArCO=cinnamoyl, p-methoxy cinnamoyl, p-N,N-dimethylamino benzoyl and combinations thereof and $R_1$=saturated or unsaturated alkyl group with carbons ranging from $C_{10}$ to $C_{22}$.

The quaternary benzamido and cinnamidopropyldimethyl alkyl ammonium tosylates of Formula I can be easily converted into vesicles by conventional methods, e.g. hydration of dry lipid film wherein the thickness of the film, temperature, time of hydration and lipid composition determine the size of the vesicles formed. Large vesicles can be converted to small vesicles or to unilamellar vesicles by high pressure homogenization or by extrusion through polycarbonate membranes. Other techniques like ether injection technique and detergent dialysis can also be employed for vesicle formation. Dispersion of these cationic UV-absorbing lipids of the present invention formed by sonication of hydrated film followed by high pressure extrusion results in vesicles of size ranging from 50 to 1000 nm. Less efficient agitation like hand shaken hydrated bilipid layer results in multilamellar large vesicles of 1 µm to 100 µm. Loaded vesicles can be prepared by incorporating a skin active or a hair active at the time of vesicle formation.

Thus, the vesicles of the present invention are used for encapsulating both hydrophobic and hydrophilic substances. The hydrophilic and hydrophobic materials include a skin active or a hair active or fragrances. A skin active is defined as any agent that exerts an effect on skin. Examples of such skin actives that can be encapsulated into liposomes of the present invention include water, organic sunscreens, anti-microbials, pesticides, moisturizers, self tanning agents, skin lightening agents, vitamins, α- and β-hydroxy acids, topical anaesthetics, anti-inflammatories, botanical extracts, enzymes like T4 endonuclease and combinations thereof.

The UV-absorbing cationic liposomes of the present invention can encapsulate salicylic acid, anti-inflammatory agents like hydrocortisone and botanical extracts like chamomile extract and skin lightening agents like arbutin. The cationic liposomes can be used to trap perfumery chemicals and fragrances as well. In summary, these UV-absorbing vesicles of the present invention can be used for encapsulating active ingredients for topical dermatological applications.

The UV-absorbing cationic vesicles can be topically applied to hair. They not only protect hair and the applied hair color from damaging UV-radiation but they also impart conditioning effect to hair strands. The liposomes of the present invention can be used for delivering active ingredients to hair follicle to treat hair disorders.

Examples of hair actives that can be encapsulated into liposomes of the present invention are organic sunscreens, oils, moisturizers, silicones, conditioners, pesticides, enzymes, anti-microbials and combinations thereof. The encapsulated fragrances can be used in hair care products. Thus, the UV sensitive fragrances can be not only protected but they are rendered substantive to hair.

This encapsulation of active ingredients serves two purposes, (i) protecting UV sensitive ingredient from UV-radiation and prolonging the shelf life of the composition and (ii) carrier for effective delivery through liposomal system. The water soluble ingredients include vitamins like ascorbic acid, sunscreens like benzophenone-4, moisturizing agents like glycerine, sodium hyaluronic acid and PVP, α-hydroxy acids. Lipid soluble active ingredients include vitamins like E, A & D and their derivatives, sunscreens like octyl methoxy cinnamate, enzymes for DNA repair like T4 endonuclease V and anti-ageing compounds like bisabolol. Other vitamins like $B_1$, $B_2$, $B_5$, $B_6$, $B_{12}$ and H can also be included in liposomes.

The vesicle compositions of the present invention are prepared by (a) formation of a film of UV-absorbing lipid, (b) hydration, (c) sonication and (d) high shear mixing. UV-absorbing cationic lipids of Formula I and other hydrophobic ingredients including skin or hair actives are dissolved in an organic solvent. The solvent is then completely evaporated on a rotary evaporator to form a thin film on the inner surface of the glass flask. This film is further subjected to high vacuum to ensure complete removal of organic solvent. The aqueous solution containing water soluble ingredients including hair and skin actives is used to hydrate the lipid film. The dispersion thus obtained is further sonicated and homogenized on a high shear homogenizer. This results in vesicles of smaller diameter ranging from 50 nm to 1000 nm.

The synthesis of UV-absorbing lipids of Formula I wherein ArCO=p-methoxy cinnamoyl or N,N-dimethylamino benzoyl and $R_1$=behenyl ($C_{22}$) and subsequent liposomal preparations (unloaded) are described in Example I and Example II. Transmission electron microscopy revealed the vesicle size to be in the range of 50 to 200 nm. Electron micrograph 1 shown in the accompanying drawings shows liposomes of p-methoxy cinnamidopropyldimethylbehenyl ammonium tosylate of Example I. The loaded vesicle compositions using UV-absorbing lipids of Formula I and various other skin actives like vitamins, sunscreens, silicones, humectants and hair actives like conditioners, silicones, anti-dandruff agents are described in Example III to VIII.

Blank liposomal preparation (without any encapsulated active ingredients) thus prepared is used in the following photoprotective experiments.

Liposomal dispersion composition (200 mg of 5.0% dispersion) of p-methoxy cinnamidopropyldimethylbehenyl ammonium tosylate and a cream preparation containing octyl methoxy cinnamate (200 mg of cream containing 5% OMC) are applied on hairless skin of inner side of forearm (36 cm$^2$). The forearms are exposed to midday sun for 15 minutes. The melanin content and erythema levels have been measured by Mexameter-18 (Courage+Khazakha, gmbh, Germany) before and after the exposure. Comparative data on Melanin and Erythema generation in Table 1 shows the superior photoprotection efficacy of liposomal preparation when compared to conventional oil/water type of emulsion containing equivalent amount of sunscreen molecule. The data collected from 20 human subjects show that liposomal preparation of cationic UV-absorbing molecule of Example I to be more effective in all the cases studied.

TABLE 1

| | Melanin Content | | Erythema Content | |
|---|---|---|---|---|
| | Octyl methoxy cinnamate (O/W cream) | p-methoxy cinnamidopropyl dimethylbehenyl ammonium tosylate (Liposomes) | Octyl methoxy cinnamate (O/W cream) | p-methoxy cinnamidopropyl dimethylbehenyl ammonium tosylate (Liposomes) |
| Before exposure | 368 | 351 | 250 | 243 |
| After exposure | 418 | 376 | 316 | 283 |
| Difference | 50 | 25 | 66 | 40 |

The cationic UV-absorbers of the present invention are found to be more effective when applied in their liposomal form than simple dispersion in water. This is established by comparing two quaternary types of UV-absorbers, one that forms vesicles and the other that does not form vesicles. p-Methoxy cinnamidopropyldimethylbehenyl ammonium tosylate forms vesicles of 50 to 200 nm size whereas p-methoxy cinnamidopropyl dimethyllauryl ammonium tosylate by itself does not form vesicles and gives unstable dispersion in water. However, this short duration of stability of aqueous suspension is sufficient for conducting the photoprotection experiment. When photoprotection efficacy is determined using these two cationic UV-absorbing lipids, p-methoxy cinnamidopropyldimethylbehenyl ammonium tosylate is found to be much more superior in protecting skin. The results are given in Table 2.

TABLE 2

| | Melanin Content | | Erythema content | |
|---|---|---|---|---|
| | p-methoxy cinnamidopropyl dimethyllauryl ammonium tosylate (suspension) | p-methoxy cinnamidopropyl dimethylbehenyl ammonium tosylate (Liposomes) | p-methoxy cinnamidopropyl dimethyllauryl ammonium tosylate (suspension) | p-methoxy cinnamidopropyl dimethylbehenyl ammonium tosylate (Liposomes) |
| Before exposure | 426 | 389 | 290 | 279 |
| After exposure | 470 | 424 | 329 | 295 |
| Difference | 44 | 35 | 39 | 16 |

The higher photoprotection efficacy of liposomal p-methoxy cinnamidopropyl dimethyl behenyl ammonium tosylate is attributed to nano size of vesicles.

EXAMPLES

The invention will now be illustrated with the help of examples. The examples are by way of illustrations only and in no way restrict the scope of invention. Many changes and modifications can be made within the scope of the present invention without departing from the spirit thereof and the invention includes all such modifications.

$^1$H NMR spectra were recorded on Varian's 300 MHz instrument and IR Spectra were recorded on Perkin Elmer's FTIR Spectrum One instrument. HPLC analysis was performed on Varian's HPLC Prostar 240.

Homogenization of aqueous dispersion was performed on a high shear homogenizer from Ystral gmbh, Germany (Model 41/G1)

TEM analysis was performed on Phillips Electron Microscope, Model CM200. Differential Scanning Calorimetry was performed on DuPont 2000 instrument.

The UV-absorbing cinnamidoalkyl and benzamidoalkyl ammonium tosylates were prepared as per the general procedure described in U.S. Pat. No. 6,613,340 (2003) and U.S. patent application Ser. No. 10/682,004 (2003).

Example I

Preparation of liposomal dispersion of p-methoxy cinnamidopropyldimethylbehenyl ammonium tosylate of Formula I, wherein ArCO=p-methoxy cinnamoyl and $R_1=C_{22}H_{45}$ A] Preparation of p-methoxy cinnamidopropyldimethylbehenyl ammonium tosylate Preparation of p-methoxy cinnamidopropyldimethylbehenyl ammonium chloride A solution of behenyl chloride (65.5 g, 190 mmol) and p-methoxy cinnamidopropyldimethyl amine (50.0 g, 190 mmol) in isopropanol (150 ml) was stirred under blanket of nitrogen at 130° C. for 12 hours. The progress of reaction was monitored by estimation of unquaternised amine. The chloride ion content and the unquaternised amidoamine were found to be 2.5% and 0.1% respectively. Distillation of isopropanol from the reaction mixture yielded the quaternary ammonium compound (115 g, 99%) as pale yellow solid.

Preparation of p-methoxy cinnamidopropyldimethylbehenyl ammonium tosylate p-Methoxy cinnamidopropyldimethylbehenyl ammonium chloride (115 g, 190 mmol) was dissolved in water (300 ml) to make 35% solution. To this stirred solution, sodium p-toluene sulphonate (37 g, 190 mmol) was added and the separated pale yellow coloured solid was subsequently washed with water, filtered and dried to yield the corresponding tosylate (131 g, 93%) as off-white solid, m.p. 50–55° C. Chloride ion was totally absent in the product.

The molar extinction coefficient, $\epsilon$ was found to be 23,000 at $\lambda$max 305 nm in methanol.

IR ($CH_2Cl_2$): 3300, 1664 $cm^{-1}$.

$^1$H NMR ($CDCl_3$, 300 MHz): δ 0.87 (3H, t, J=6.3 Hz), 1.18 (34H, broad signal), 1.58 (2H, unresolved multiplet), 2.10 (2H, unresolved multiplet), 2.32 (3H, singlet, methyl of tosyl), 3.13 (6H, singlet, two methyl on nitrogen), 3.20 (2H, unresolved multiplet), 3.45 (2H, unresolved multiplet), 3.68 (2H, unresolved multiplet), 3.78 (3H, singlet, OCH$_3$), 6.52 (1H, d, J=15.6 Hz), 6.76 (2H, d, J=8.4 Hz), 7.14 (2H, d, J=6.0 Hz), 7.31 (2H, d, J=8.6 Hz), 7.48 (1H, d, J=15.6 Hz), 7.78 (2H, d, J=7.8 Hz).

The p-methoxy cinnamidopropyldimethylbehenyl ammonium tosylate was analysed on HPLC using ion-pairing technique. The mobile phase employed for ion-pairing comprised of 0.1 M octane sulphonic acid in aqueous methanol (80:30). Reversed phase column Chromspher C$_8$ was used with mobile phase flow rate of 1.0 ml/min. The detection was done at 280 nm. The purity of final compound from this analysis was found to be 99.8%.

B] Preparation of Liposomal Dispersion p-Methoxy cinnamidopropyldimethylbehenyl ammonium tosylate (200 mg) was dissolved in dichloromethane (10 ml). The solvent was evaporated off on a rotary evaporator to form a thin film of quaternary ammonium tosylate. It was then kept under reduced pressure for 10 minutes to ensure complete removal of traces of the solvent. The thin film that was formed on the inner surface of glass flask was hydrated using water (100 ml) and sonicated for 1 hour. The sonicated dispersion was further homogenized by passing through high sheer homogenizer from Ystral gmbh, Germany (Model no. 41/G1) for 2 hours.

Transmission Electron Microscopy Analysis

Figure 5:
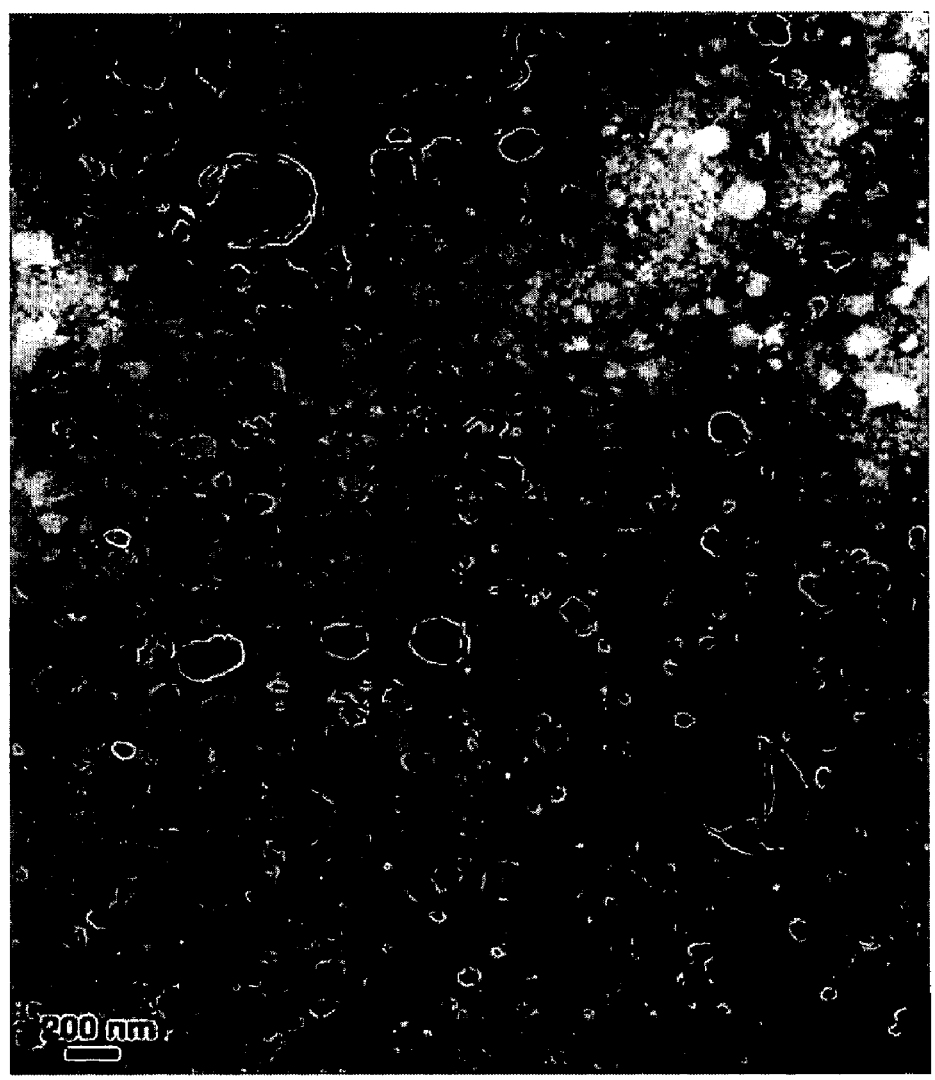

One drop of above dispersion was placed on a carbon coated copper grid. It was stained with saturated solution of uranyl acetate for one minute. The grid was then air dried and subsequently it was dried under vacuum. The TEM analysis confirmed the formation of vesicles (FIG. 5). The size of liposomes ranges from 50 nm to 200 nm.

Differential Scanning Calorimetry Analysis

Differential Scanning Calorimetry curve for dilute dispersion (1.5%) of p-methoxy cinnamidopropyldimethylbehenyl ammonium tosylate showed endothermic peak at 43.6° C. indicating that this is the phase transition temperature from gel to liquid crystalline state.

Example II

Preparation of liposomal dispersion of p-N,N-dimethylamine benzamidopropyldimethylbehenyl ammonium tosylate ArCO=p-N,N-dimethylamino benzoyl and R$_1$=C$_{22}$H$_{45}$ A] Preparation of p-N,N-dimethylamine benzamidopropyldimethylbehenyl ammonium tosylate It was prepared by reacting p-N,N-dimethylamino benzamidopropyldimethylamine, behenyl chloride and sodium p-toluene sulphonate according to literature procedure (U.S. Pat. No. 5,427,773 (1995).

Preparation of p-N,N-dimethylamino benzamidopropyldimethylbehenyl ammonium chloride Behenyl chloride (14 g, 40 mmol) and p-N,N-dimethylamino benzamidopropyldimethylamine (10.0 g, 40 mmol) was stirred under blanket of nitrogen at 150° C. for 15 hours. The progress of reaction was monitored by estimation of unquaternised amine. At the end of the reaction, chloride ion and free amidoamine was found to be 5.9% and 0.3% respectively. The reaction yielded the quaternary ammonium compound (23.0 g, 96%) as pale yellow solid.

b) Preparation of p-N,N-dimethylamine benzamidopropyldimethylbehenyl ammonium tosylate p-N,N-dimethylamino benzamidopropyldimethylbehenyl ammonium chloride (23 g, 39 mmol) was dissolved in water (50 ml) to make 30% solution. To this stirred solution, sodium p-toluene sulphonate (8 g, 41 mmol) was added and the separated pale yellow coloured solid upon heating on a water-bath for 15 minutes was subsequently washed with water, filtered and dried to yield the corresponding tosylate (26 g, 93%) as off-white solid, m.p. 54–57° C. Chloride ion was totally absent in the product.

The molar extinction coefficient, ∈ was found to be 22,200 at λmax 305 nm in methanol.

IR (CH$_2$Cl$_2$): 1608, 1636, 3427 cm$^{-1}$.

$^1$H NMR (CDCl$_3$, 300 MHz): δ 0.88 (3H, t, J=6.3 Hz), 1.06–1.44 (40H, broad signal), 2.01 (2H, unresolved multiplet), 2.30 (3H, s, methyl of tosyl), 2.91 (6H, s), 3.01 (6H, s), 3.06 (2H, unresolved multiplet), 3.44 (1H, s), 3.46 (2H, t), 3.65 (2H, t), 6.47 (2H, d, J=8.7 Hz), 7.11 (2H, d, J=8.1 Hz), 7.73 (2H, d, J=8.1 Hz), 7.73 (2H, d j=8.1 Hz), 7.83 (2H, d, J=9.3 Hz).

The final compound was analysed on HPLC using ion-pairing technique. The mobile phase employed for ion-pairing comprised of 0.1 M octane sulphonic acid in aqueous methanol (90:10). Reversed phase column Chromspher C$_8$ was used with mobile phase flow rate of 1.0 ml/min. The detection was done at 280 nm. The purity of final compound from this analysis was found to be 99.8%.

B] Preparation of Liposomal Dispersion p-N,N-dimethyl benzamidoropyldimethylbehenyl ammonium tosylate (200 mg) was dissolved in dichloromethane (10 ml). The solvent was evaporated off on a rotary evaporator to form a thin film of quaternary ammonium tosylate. It was then kept under reduced pressure for 10 minutes to ensure complete removal of traces of the solvent. The thin film that was formed on the inner surface of glass flask was hydrated using water (100 ml) and sonicated for 1 hour. The sonicated dispersion was further homogenized by passing through high sheer homogenizer from Ystral gmbh, Germany (Model no. 41/G1) for 2 hours. The TEM analysis confirmed the formation of vesicles. The size of liposomes was found to be between 50 nm to 200 nm.

Example III

Preparation of Non-Greasy Skin Protective Formulation

| Ingredients | % w/w |
|---|---|
| p-methoxy cinnamidopropyl dimethyl behenyl ammonium tosylate | 10.0 |

-continued

| Ingredients | % w/w |
|---|---|
| Vitamin E acetate | 1.0 |
| Ascorbic acid | 1.0 |
| Niacinamide | 1.0 |
| Methoxy t-butyl dibenzoyl methane | 1.0 |
| Laureth-3 | 2.0 |
| 2-phenoxyethanol | q.s |
| Fragrance | q.s |
| Water | q.s to 100% |

The non-greasy skin protective composition was prepared as follows:

p-Methoxy cinnamidopropyl dimethyl behenyl ammonium tosylate (10 g), vitamin E acetate (1.0 g), methoxy t-butyl dibenzoyl methane (1.0 g), laureth-3 (2.0 g) and fragrance were dissolved in dichloromethane (30 ml). The solvent was then evaporated on a rotary evaporator to form a thin film on the inner surface of a round bottom flask. The flask with the film was subjected to high vacuum (0.01 mm of Hg) to remove last traces of solvent. The dried film was then hydrated with water (84 ml) containing ascorbic acid (1.0 g), niacinamide (1.0 g) and 2-phenoxyethanol and the whole was sonicated for 2 hours. The sonicated dispersion was further homogenized for 2 hours. The resulting dispersion had vesicles with diameter of 1000 nm.

Example IV

Preparation of Protective Hair Conditioner

| Ingredients | % w/w |
|---|---|
| p-methoxy cinnamidopropyl dimethyl behenyl ammonium tosylate | 10.0 |
| Distearyl dimonium chloride | 5.0 |
| Dimethicone copolyol (SF-1288, GE Silicones) | 1.0 |
| Laureth-3 | 2.0 |
| 2-phenoxyethanol | q.s |
| Fragrance | q.s |
| Water | q.s to 100% |

The protective hair conditioner was prepared as follows:

p-methoxy cinnamidopropyl dimethyl behenyl ammonium tosylate (10 g), distearyl dimonium chloride (5.0 g), laureth-3 (2.0 g) and fragrance were dissolved in dichloromethane (30 ml). The solvent was then evaporated on a rotary evaporator to form a thin film on the inner surface of a round bottom flask. The flask with the film was subjected to high vacuum (0.01 mm of Hg) to remove last traces of solvent. The dried film was then hydrated with water (82 ml) containing dimethicone copolyol (SF-1288, GE Silicones) (1.0 mg), and 2-phenoxyethanol and the whole was sonicated for 2 hours. The sonicated dispersion was further homogenized for 2 hours. The average vesicle size was found to be 5 µm.

Example V

Preparation of Protective Hair Conditioner

| Ingredients | % w/w |
|---|---|
| p-methoxy cinnamidopropyl dimethyl behenyl ammonium tosylate | 10.0 |
| Polyquaternium-7 | 1.0 |
| Dimethicone copolyol (SF-1288, GE Silicones) | 1.0 |
| Laureth-3 | 4.0 |
| 2-phenoxyethanol | q.s |
| Fragrance | q.s |
| Water | q.s to 100% |

The protective hair conditioner was prepared as follows:

p-Methoxy cinnamidopropyl dimethyl behenyl ammonium tosylate (10 g), laureth-3 (4.0 g) and fragrance were dissolved in dichloromethane (3 ml). The solvent was then evaporated on a rotary evaporator to form a thin film on the inner surface of a round bottom flask. The flask with the film was subjected to high vacuum (0.01 mm of Hg) to remove last traces of solvent. The dried film was then hydrated with water (84 ml) containing dimethicone copolyol (SF-1288, GE Silicones) (1.0 g), polyquaternium-7 (1.0 g) and 2-phenoxyethanol and the whole was sonicated for 2 hours. The sonicated dispersion was further homogenized for 2 hours. The average vesicle size was found to be 1000 nm.

Example VI

Preparation of Protective Hair Conditioner

| Ingredients | % w/w |
|---|---|
| p-methoxy cinnamidopropyl dimethyl behenyl ammonium tosylate | 10.0 |
| Cetyl trimethyl ammonium chloride | 6.0 |
| Laureth-3 | 4.0 |
| 2-phenoxyethanol | q.s |
| Fragrance | q.s |
| Water | q.s to 100% |

The protective hair conditioner was prepared as follows:

p-Methoxy cinnamidopropyl dimethyl behenyl ammonium tosylate (10 g), laureth-3 (4.0 g) and fragrance were dissolved in dichloromethane (30 ml). The solvent was then evaporated on a rotary evaporator to form a thin film on the inner surface of a round bottom flask. The flask with the film was subjected to high vacuum (0.01 mm of Hg) to remove last traces of solvent. The dried film was then hydrated with water (80 ml) containing cetyl trimethyl ammonium chloride (6.0 g) and 2-phenoxyethanol and the whole was sonicated for 2 hours. The sonicated dispersion was further homogenized for 2 hours. This dispersion had vesicles whose diameters were found to be between 500 nm to 1 µm.

Example VII

Preparation of Hair Protective Formulation with Anti-Dandruff Agent

| Ingredients | % w/w |
|---|---|
| p-methoxy cinnamidopropyl dimethyl behenyl ammonium tosylate | 10.0 |
| Laureth-3 | 5.0 |
| Octopirox (Pyroctone) | 1.0 |
| 2-phenoxyethanol | q.s |
| Fragrance | q.s |
| Water | q.s to 100% |

The hair protective formulation with anti-dandruff agent was prepared as follows:

p-Methoxy cinnamidopropyl dimethyl behenyl ammonium tosylate (10 g), laureth-3 (5.0 g), Octopirox (1.0 g) and fragrance were dissolved in dichloromethane (30 ml). The solvent was then evaporated on a rotary evaporator to form a thin film on the inner surface of a round bottom flask. The flask with the film was subjected to high vacuum (0.01 mm of Hg) to remove last traces of solvent. The dried film was then hydrated with water (84 ml) containing 2-phenoxyethanol and the whole was sonicated for 2 hours. The sonicated dispersion was further homogenized for 2 hours. The average vesicle size was found to be 1 to 5 µm.

Example VII

Preparation of Skin Protective Formulation with Humectant (Conditioning Agent)

| Ingredients | % w/w |
|---|---|
| p-methoxy cinnamidopropyl dimethyl behenyl ammonium tosylate | 10.0 |
| Laureth-3 | 10.0 |
| Polyglycerol stearate | 10.0 |
| Sorbitol | 3.0 |
| Polyglycerol-10 | 3.0 |
| 2-phenoxyethanol | q.s |
| Fragrance | q.s |
| Water | q.s to 100% |

The skin protective formulation with humectant (conditioning agent) was prepared as follows:

p-Methoxy cinnamidopropyl dimethyl behenyl ammonium tosylate (10 g), laureth-3 (10 g), polyglycerol stearate (10 g) and fragrance were dissolved in dichloromethane (30 ml). The solvent was then evaporated on a rotary evaporator to form a thin film on the inner surface of a round bottom flask. The flask with the film was subjected to high vacuum (0.01 mm of Hg) to remove last traces of solvent. The dried film was then hydrated with water (64 ml) containing sorbitol (3.0 g), polyglycerol-10 (3.0 g) and 2-phenoxyethanol and the whole was sonicated for 2 hours. The sonicated dispersion was further homogenized for 2 hours. The average vesicle size was found to be 1 to 5 µm.

What has been described herein is the descriptive of the preferred embodiments of this invention. It is not meant in any way to limit the scope and spirit of this invention.

ADVANTAGES OF THE INVENTION

To create sun protection formulations of higher photoprotection efficacy has been an active area of research world over. Liposomal compositions based on natural or synthetic lipids for effective delivery of cosmetic actives are already in vogue. Although liposome technology is forty years old, vesicles made from conventional lipids like phospholipids, glycolipids, ceramides and organic sunscreens for skin and hair protections have not been very successful because of low loading of the payload. This difficulty is overcome by the vesicles of the present invention because they are made from UV-absorbing lipids.

Thus, the main advantage of the vesicular compositions of the present invention is that these vesicles of cationic UV-absorbing lipids offer high level of photoprotection to skin and hair by virtue of their vesicular form and substantive nature. The second advantage of these vesicles is that they can encapsulate both hydrophilic and hydrophobic active ingredient and increase their efficacy via liposomal delivery. The third advantage of these vesicles is that since they are derived from UV-absorbing lipids they photoprotect the encapsulated ingredients from damaging effect of UV radiation and thereby extend the shelf life of UV sensitive ingredients. Another advantage is, unlike vesicles made from naturally occurring lipids, vesicles made from quaternary ammonium lipids of the present invention are not susceptible to microbial attack.

In summary, higher photoprotection is the result of vesicular nature of the composition, cationic nature of vesicles, UV-absorbing property of lipids, nano size of liposomes and effective delivery of other actives.

What is claimed is:

1. A vesicle (liposome) composition for hair and skin care comprising cationic UV-absorbing lipids of Formula I,

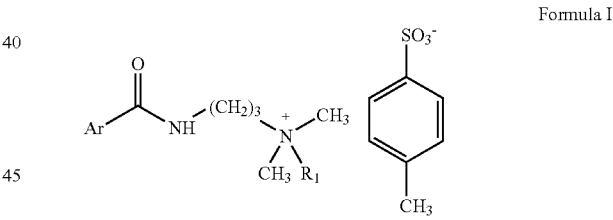

Formula I such that in the said formula I ArCO is selected from cinnamoyl, p-methoxy cinnamoyl, p-N,N-dimethylamino benzoyl and combinations thereof and $R_1$=saturated or unsaturated alkyl group with carbons ranging from $C_{10}$ to $C_{22}$, wherein the diameter of the said vesicles range from 50 nm to 20 µm, wherein the said vesicles are substantive to hair and skin and are with or without skin actives or hair actives, wherein the said lipid vesicles encapsulate aqueous phase, wherein the UV-absorbing cationic lipids content is between 0.1 to 20% by weight.

2. A vesicle composition of claim 1, wherein, encapsulated skin active is selected from organic sunscreens, salicylic acid, moisturizers, skin tanning agents, vitamins, hydroxy acids, steroidal, and non-steroidal anti-inflammatories, enzymes, proteins, topical anesthetics, botanical extracts, genetic material, fragrances and mixtures thereof.

3. A vesicle composition of claim 1, further comprising additives selected from fatty alcohol ethoxylates, alkyl polyglycerols, sterols, ceramides and phospholipids.

4. A vesicle composition of claim 1, wherein, encapsulated hair active is selected from anti-dandruff agents, hair conditioners, organic sunscreens, silicones, silicone ethoxylates, oils, moisturizers, botanical extracts, fragrances and mixtures thereof.

5. A process for preparing a vesicle (liposome) composition for hair and skin care comprising cationic UV-absorbing lipids of Formula I,

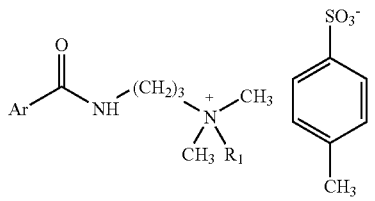

Formula I such that in the said formula I ArCO is selected from cinnamoyl, p-methoxy cinnamoyl, p-N,N-dimethylamino benzoyl and combinations thereof and $R_1$=saturated or unsaturated alkyl group with carbons ranging from $C_{10}$ to $C_{22}$, wherein the diameter of the said vesicles range from 50 nm to 20 μm, wherein the said vesicles are substantive to hair and skin and are with or without skin actives or hair actives, wherein the said lipid vesicles encapsulate aqueous phase, wherein the UV-absorbing cationic lipids content is between 0.1 to 20% by weight, said process comprising (a) dispersing the cationic UV-absorbing lipid in water or buffer solution by sonication and (b) subjecting the dispersion to high shear mixing.

6. A vesicle (liposome) composition for hair and skin care from cationic UV-absorbing lipids of Formula I when made by the process of claim 5.

* * * * *